(12) United States Patent
Johnson et al.

(10) Patent No.: US 6,661,240 B1
(45) Date of Patent: Dec. 9, 2003

(54) METHODS AND SYSTEMS FOR CAPACITIVE MOTION SENSING AND POSITION CONTROL

(75) Inventors: Mark A. Johnson, Charlton, NY (US); Vivek Bhatt, Wauwatosa, WI (US)

(73) Assignee: General Electric Co., Schenectady, NY (US)

( * ) Notice: Subject to any disclaimer, the term of this patent is extended or adjusted under 35 U.S.C. 154(b) by 92 days.

(21) Appl. No.: 09/678,916

(22) Filed: Oct. 4, 2000

(51) Int. Cl.[7] .......................... G01R 27/26; A61B 5/117
(52) U.S. Cl. ..................... 324/662; 324/658; 600/595
(58) Field of Search ................ 324/658, 207.21, 324/662, 754; 318/568.21; 361/283.1; 378/91, 95, 117; 600/483, 484, 528–529, 534–535, 595

(56) References Cited

U.S. PATENT DOCUMENTS

| | | | | |
|---|---|---|---|---|
| 3,875,481 A | * | 4/1975 | Miller et al. | 361/283.1 |
| 4,093,915 A | * | 6/1978 | Briefer | 324/658 |
| 4,320,766 A | * | 3/1982 | Alihanka et al. | 361/283.1 |
| 4,939,456 A | * | 7/1990 | Morelli et al. | 324/207.21 |
| 5,002,060 A | * | 3/1991 | Nedivi | 600/484 |
| 5,097,495 A | * | 3/1992 | Gray et al. | 378/117 |
| 5,105,455 A | * | 4/1992 | Kato et al. | 378/117 |
| 5,170,127 A | * | 12/1992 | Henley | 324/754 |
| 5,265,609 A | * | 11/1993 | Buchanan et al. | 600/595 |
| 5,319,977 A | * | 6/1994 | Quate et al. | 324/662 |
| 5,539,292 A | * | 7/1996 | Vranish | 318/568.21 |
| 5,651,044 A | | 7/1997 | Klotz, Jr. et al. | |
| 5,805,664 A | * | 9/1998 | Whipple, III et al. | 378/117 |
| 5,861,583 A | | 1/1999 | Schediwy et al. | |
| 5,989,193 A | * | 11/1999 | Sullivan | 600/529 |
| 6,066,954 A | | 5/2000 | Gershenfeld et al. | |
| 6,119,033 A | * | 9/2000 | Spigelman et al. | 600/426 |
| 6,129,686 A | * | 10/2000 | Friedman | 600/595 |
| 6,188,228 B1 | * | 2/2001 | Philipp | 324/658 |
| 6,239,389 B1 | | 5/2001 | Allen et al. | |
| 6,281,797 B1 | | 8/2001 | Forster et al. | |
| 6,293,150 B1 | | 9/2001 | Conlan | |
| 6,295,881 B1 | | 10/2001 | Stewart | |
| 6,304,091 B1 | | 10/2001 | Shahoian | |
| 6,541,973 B1 | * | 4/2003 | Danby et al. | 324/318 |
| 6,556,695 B1 | * | 4/2003 | Packer et al. | 382/128 |

\* cited by examiner

*Primary Examiner*—Kamand Cuneo
*Assistant Examiner*—Jermele Hollington
(74) *Attorney, Agent, or Firm*—Robert B. Reeser, III; Armstrong Teasdale LLP

(57) ABSTRACT

A system for detecting motion and proximity by determining capacitance between a sensor and an object. The sensor includes sensing surfaces made of a thin film of electrically conductive material mounted on a non-conductive surface. In another embodiment, the sensor is a human body. The sensor senses the capacitance between a sensor's surface and an object in its vicinity and provides the capacitance to a control system that directs machine movement. Because the sensor does not require direct contact or line-of-sight with the object, a machine can be controlled before harm occurs to the object.

14 Claims, 6 Drawing Sheets

METHODS AND SYSTEMS FOR CAPACITIVE MOTION SENSING AND POSITION CONTROL

BACKGROUND OF THE INVENTION

This invention relates generally to devices used to provide safety for humans in proximity with moving equipment, and more specifically to motion and proximity sensors employed as part of a control system to orient equipment based on capacitance.

Safety is important when people are close to moving machines. One such example is locally controlled machines or robotic equipment where people are in close proximity to moving mechanical components. Another example is in the medical imaging equipment industry.

In known systems, conventional safety mechanisms such as mechanical switches and fluid-filled bladders connected to pressure switches are typically mounted directly to the moving mechanical components, or in proximity of the hazardous area. These conventional safety mechanisms require direct contact between the person or inanimate object and the safety mechanism to operate. For example, the fluid-filled bladder mounted to a moving mechanical component uses a pressure sensor or a pressure switch inside the bladder to detect increased pressure as the bladder makes contact with an object. The sensed pressure increase typically is an input to a control system which stops the moving mechanical component.

In other known systems, plates, levers, cables, and rings are connected to mechanical switches and mounted on the moving mechanical component. The switches are activated when the plate, lever, cables, or ring contacts the person or object, and the machine is stopped before any harm occurs.

Disadvantages of the above described systems include expense (fluidfilled bladders) and the fact that the sensing area is highly localized (mechanical switches). Such devices are typically ON or OFF and therefore provide no information to the control system regarding relative distance between the subject and the sensor. systems. The drawback to those systems is that an unobstructed line-of-sight between the detector and the subject is required. As applied to medical imaging equipment, required sterile covers and drapes preclude use of line-of-sight proximity detector systems. Depending on the implementation specifics, these sensors are also highly directional and impacted by object properties such as reflectivity and specularity, which further limits their applicability.

In the listed examples, safety cannot be enhanced, nor injury prevented simply by increasing the distances between man and machine because each example requires close proximity between man and machine. It would therefore be desirable to provide a system whereby proximity and relative distance to a person or an object can be sensed and the information regarding proximity and distance used to control movement and prevent contact with the person or object and thereby increase the safety of such a system.

BRIEF SUMMARY OF THE INVENTION

In one aspect, the present invention relates to a method and system for detecting motion using a capacitance between a sensor and an object. Alternatively, the invention detects proximity of an object using the capacitance between a sensor and the object. In an exemplary embodiment, a capacitance based proximity sensor is used as a detector. The sensor includes sensing surfaces made of a thin film of electrically conductive material mounted on a nonconductive surface. The nonconductive surface can take any shape and form. The sensor senses the capacitance between a conductive surface and an object placed in its vicinity, and the sensor provides a capacitance value to a control system. The control system is programmed to use the capacitance data to control the movement of a machine or piece of equipment. In one embodiment, the piece of equipment is a medical imaging system.

In another embodiment, the sensing surface is a human body. A relative capacitance between the human body and surrounding objects is determined. The control system uses the capacitance information to determine a position of the body and proximity of objects near the body to control movement of a machine or piece of equipment.

Accordingly, because the sensor can take any size and shape, and does not require direct contact or line-of-sight with the object to determine if an object has moved, a machine or piece of equipment can be controlled before harm occurs to the object.

DETAILED DESCRIPTION OF THE INVENTION

Figure 1:
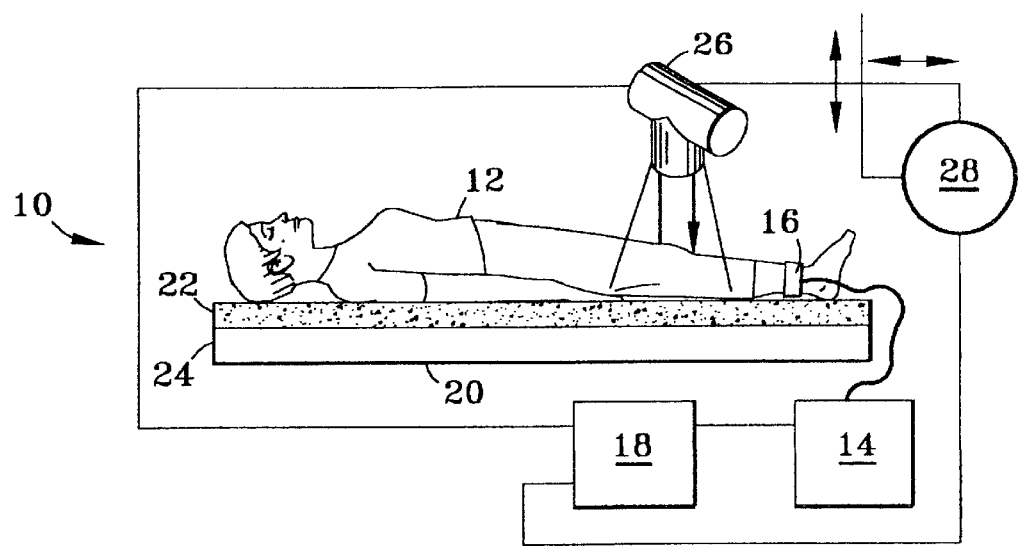
FIG. 1 is a diagram showing a system for detecting capacitance change based upon movement.

FIG. 1 is a diagram showing a system 10 for detecting capacitance change based upon movement of, or proximity to, an object 12. Object 12 is connected to a capacitance sensing circuit 14 via a conductive strap 16. Sensing circuit 14 senses capacitance and supplies data relating to the measured capacitance to control system 18. Object 12 is on a surface 20 which includes a non-conductive surface 22 such as a film or mat placed upon a conductive surface 24. Control system 18 is programmed to use the measured capacitance data to control movement of component 26 in both horizontal and vertical axes via a motor 28. Component 26 in one embodiment is a radiation source. Component 26 in an alternative embodiment is a detector. Component 26 in a further alternate embodiment is a sensor. Component 26 in a still further embodiment is a nuclear medicine imaging source. Component 26 in another embodiment is a laser source. Component 26 in yet another embodiment is a component of a medical system, e.g., computer aided tomography (CAT), magnetic resonance imaging (MRI), computed tomography (CT), digital fluoroscopy, positron emission tomography (PET), positron emission transaxial tomography (PETT), and mammography.

The amount of capacitance sensed by circuit 14 changes as object 12 moves. In another embodiment, the capacitance sensed also changes as a proximity of object 12 changes with respect to component 26. The change in capacitance is received by control system 18 which in turn causes changes in predetermined movement of component 26 such that the trajectory of object 26 is optimized for a procedure being performed. An ability to detect unexpected motion of object 12 provides control system 18 or an operator of control system 18 with a signal to slow or stop movement of component 26 to prevent injury to object 12 or damage to the above described equipment. Capacitance sensing circuit 14 is capable of measuring small changes (15–30 femtoFarads) in capacitance. Since an object 12 changes capacitance as object 12 moves, raising of arms, crossing of legs, finger wiggling, toe wiggling, and torso motion are all detectable.

Capacitance sensing circuit 14 uses charge transfer technology to measure the capacitance of object 12 connected to circuit 14. Conductive strap 16 is used, along with circuit 14 to measure an effective nominal capacitance of object 12. Capacitance sensing circuit 14 is manually or automatically re-calibrated for new nominal capacitive loads, such as, for example a different object 12. The re-calibration process changes the nominal capacitance about which small changes, such as the movement of object 12 described above, are detected. Re-calibration allows system 10 to accommodate objects 12 of different sizes, shapes, clothing, and body hair, for example. Re-calibration also can take into account the environment object 12 is placed, such as temperature and relative humidity.

Figure 2:
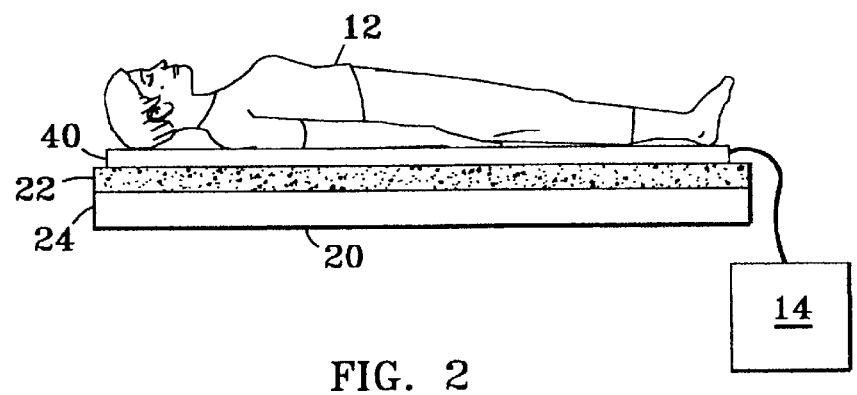
FIG. 2 is a diagram showing an alternative system for detecting capacitance based upon movement.

FIG. 2 shows an alternative embodiment to the system shown in FIG. 1 employing an alternative method for the measurement of capacitance. Non-conductive surface 22 and conductive surface 24 are as described above, however, a conductive mat 40 is placed on top of non-conductive surface 22 and is electrically connected to capacitive sensing circuit 14. The measured capacitance is based upon an amount of object 12 actually touching conductive mat 40, as well as movement of object 12, such as raising of arms, crossing of legs, finger wiggling, toe wiggling, and torso motion. For instance, the measured capacitance of a human body laying supine on mat 40 will be greater than the measured capacitance of a human body laying supine on mat 40 with both legs bent and the soles of the feet resting flat on mat 40. As object 12 moves and less of the body is touching mat 40, the measured capacitance will decrease. The larger the surface area touching mat 40, the higher the capacitance.

The embodiments shown in FIGS. 1 and 2 demonstrate, for example, how a human body, can be used as a detector for a capacitive sensing circuit. Measured capacitance depends on the location of objects relative to the body, and other objects or persons near the subject being used as a detector can be detected. Using a subject as a detector may be ideal when there is the potential for a number of moving components to make contact with the subject, a sensor being installed on every moving component being unfeasible.

Figure 3:
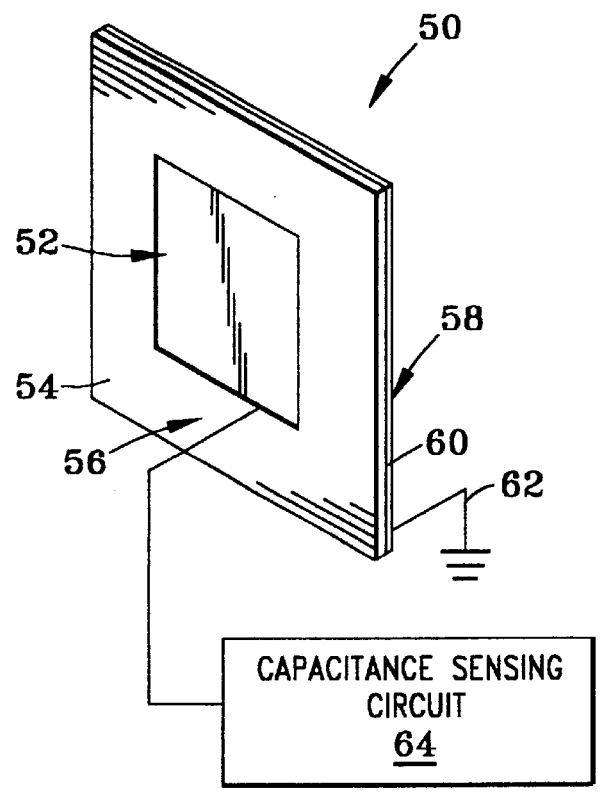
FIG. 3 is a diagram showing one embodiment of a capacitance based proximity sensor.

FIG. 3 is a diagram showing one embodiment of a capacitance based proximity sensor 50 used in systems where the subject is not used as the detector. Sensor 50 includes a sensing surface 52 which is made of a thin film of conducting material mounted on a front side 54 of non-conductive backing material 56. A backing surface 58 of electrically grounded thin film conducting material mounted on a back side 60 of non-conductive backing material 56 completes the sensor. As stated above, backing surface 58 is connected to an electrical ground 62. Sensing surface 52 is electrically connected to a capacitive sensing circuit 64 and as shown in FIG. 3, may be configured to be of a size smaller in surface area than that of backing material 56.

Figure 4:
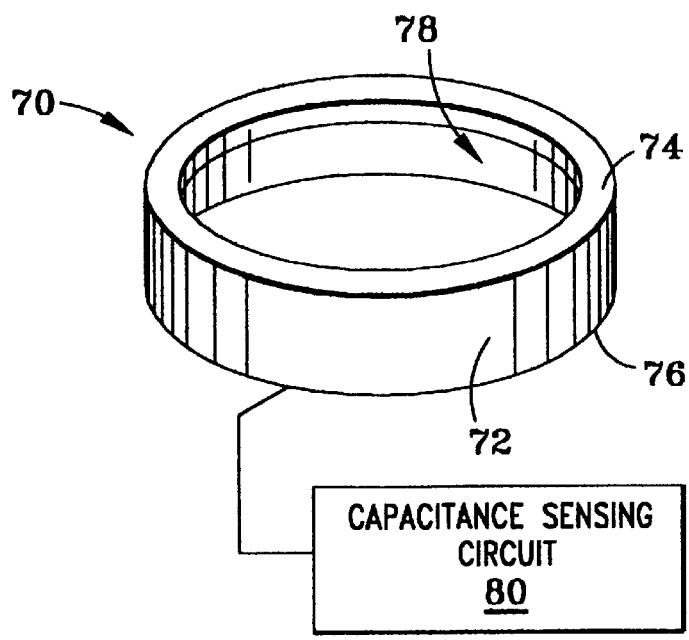
FIG. 4 is a diagram showing an alternative embodiment of a capacitance based proximity sensor.

FIG. 4 is a diagram showing an alternative embodiment of a capacitance based proximity sensor 70. Sensor 70 is cylindrically shaped and consists of sensing surfaces 72, 74 and 76 of the thin film electrically conductive material. Sensing surface 72 covers an outer surface of sensor 70 and sensing surfaces 74 and 76 cover end surfaces of the cylinder, a top surface and a bottom surface respectively.

Non-conductive backing material 78 is the "body" of the cylinder, giving sensor 70 strength and a surface for the mounting of surfaces 72, 74 and 76 which are electrically connected to a capacitive sensing circuit. A backing surface (not shown) is electrically connected to ground. In another embodiment, the backing surface is not utilized by sensor 70.

Figure 5:
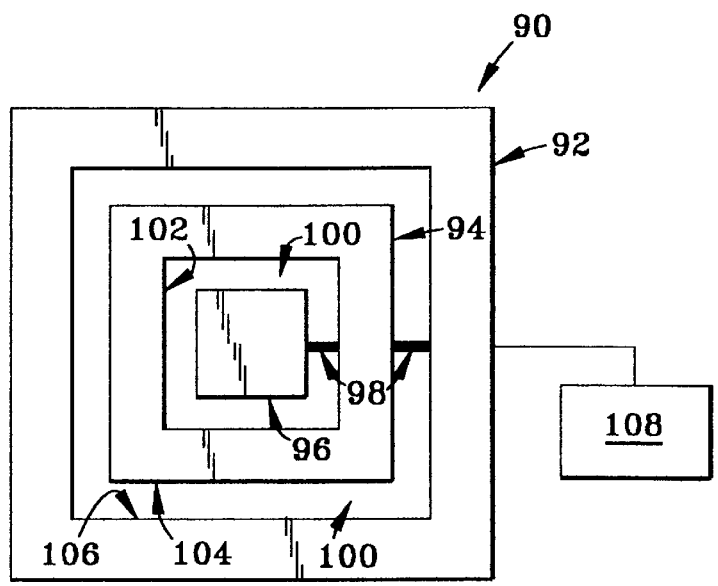
FIG. 5 is a diagram of a third embodiment of a capacitance based proximity sensor.

FIG. 5 is a diagram of one embodiment of a proximity sensor 90 configured to shape the sensing field. Sensor 90, in the embodiment shown in FIG. 5 consists of an outer sensing surface 92, a central sensing surface 94, and an inner sensing surface 96. Outer sensing surface 92, central sensing surface 94 and inner sensing surface 96 are electrically connected with conductive strips 98 to form an electrically continuous circuit and are mounted on non-conductive backing material 100. In one exemplary embodiment, sensor 90 has sensing surface dimensions where inner sensing surface 96 has a dimension of 3 cm×3 cm, a space of 3 cm separates inner sensing surface 96 from an inner circumference 102 of central sensing surface 94 which is 3 cm wide. Another 3 cm gap in sensing material separates an outer circumference 104 of central sensing surface 94 from an inner circumference 106 of outer sensing surface 92. Outer sensing surface 92 is 3 cm in width. In the exemplary embodiment, backing material 100 is fabricated from mylar, which is virtually invisible to x-ray radiation. The thickness of the mylar backing depends on mechanical strength requirements of an application. The sensing surfaces of sensor 90 are variable in size and in number in order to shape the sensing field of sensor 90 and are connected to a capacitive sensing circuit 108. In the exemplary embodiment, sensing surfaces 92, 94 and 96 of sensor 90 are fabricated from 3 um thick aluminum foil and bonded to the mylar. In another embodiment, aluminum plates are bonded to the mylar. To be invisible to a vascular spectrum, surfaces 92, 94 and 96 are fabricated from aluminum foil/plates less than 5 um in thickness. In a further embodiment, sensing surfaces 92, 94 and 96 are fabricated from copper. In a still further embodiment, sensing surfaces 92, 94 and 96 are fabricated from tin.

Figure 6:
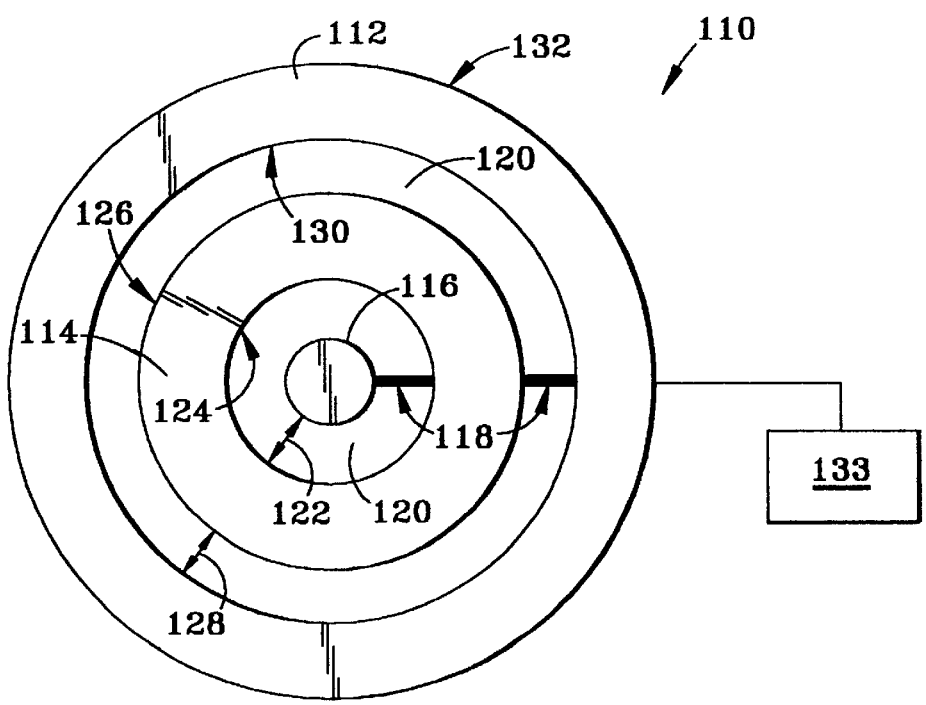
FIG. 6 is a diagram of a fourth embodiment of a capacitance based proximity sensor.

FIG. 6 is a diagram of an alternative circular embodiment of a proximity sensor configured to shape the sensing field. Sensor 110, in the embodiment shown in FIG. 6 consists of an outer sensing surface 112, a central sensing surface 114, and an inner sensing surface 116. Outer sensing surface 112 and central sensing surface 114 are ring shaped. Inner sensing surface 116 is circularly shaped. Outer sensing surface 112, central sensing surface 114, and inner sensing surface 116 are electrically connected with conductive strips 118 to form an electrically continuous circuit and are mounted on non-conductive backing material 120. In one exemplary embodiment, sensor 110 has sensing surface dimensions where inner sensing surface 116 has a diameter of 3 cm. A ring shaped space 122 that is 3 cm wide separates inner circular sensing surface 116 from central sensing surface 114. Central circular sensing surface 114 has a inner ring 124 and an outer ring 126. Inner ring 124 has a diameter of 9 cm and outer ring 126 has a diameter of 12 cm, such that central sensing surface 114 has a sensor ring area of 3 cm in diameter. Another 3 cm wide ring shaped space 128 in sensing material separates central sensing surface 114 from outer sensing surface 112. Outer sensing surface 112 has an inner ring 130 and an outer ring 132. Inner ring 130 has a diameter of 21 cm and outer ring 132 has a diameter of 27 cm, such that outer sensing surface 112 has a sensor ring area of 3 cm in diameter. In the exemplary embodiment, backing material 120 is fabricated from mylar, which is virtually invisible to x-ray radiation. The thickness of the mylar backing depends on mechanical strength requirements of an application. The sensing surfaces of sensor 110 are variable in size and in number in order to shape the sensing field of sensor 110 and are connected to a capacitive sensing circuit 133. In the exemplary embodiment, sensing surfaces 112, 114 and 116 of sensor 110 are fabricated from 3 um thick aluminum foil and bonded to the mylar. In another embodiment, aluminum plates are bonded to the mylar. To be invisible to a vascular spectrum, surfaces 112, 114 and 116 are fabricated from aluminum foil/plates less than 5 um in thickness. In a further embodiment, sensing surfaces 112, 114 and 116 are fabricated from copper. In a still further embodiment, sensing surfaces 112, 114 and 116 are fabricated from tin.

Figure 7:
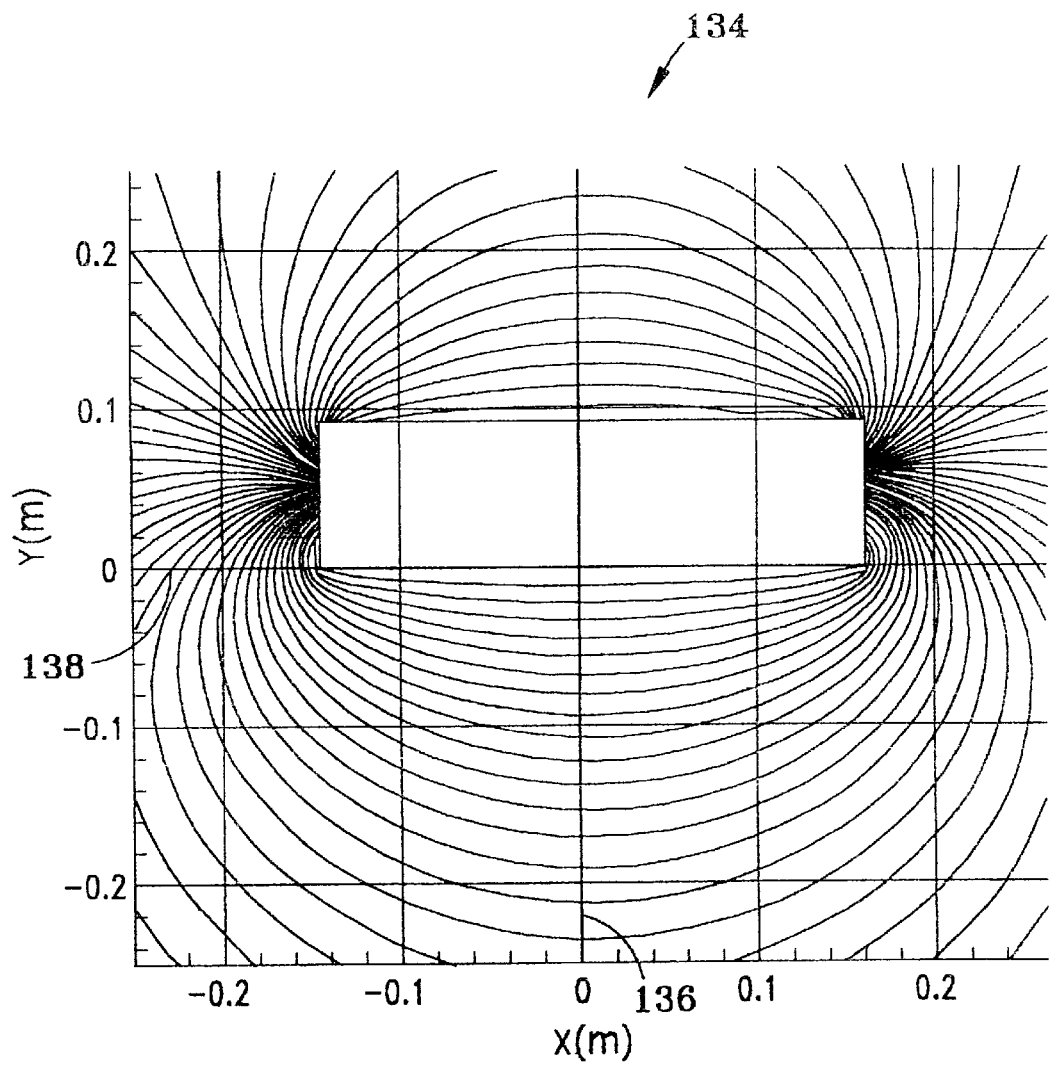
FIG. 7 is a diagram of a sensing field for a capacitance based proximity sensor.

FIG. 7 is a diagram 134 of a sensing field for a capacitance based proximity sensor where no shaping has been employed, for example, where the sensing surface is a solid rectangular or square thin-film conductor. Such a sensor is able to detect capacitive changes omni-directionally. The sensor which produces the type of field shown in FIG. 7 is more sensitive to objects which approach the sensor along an x=0 axis 136 and less sensitive to objects approaching along a y=0 axis 138. Objects moving along axis 136 are detected more quickly and from a farther distance. This non-uniform sensitivity is not particularly desirable.

Figure 8:
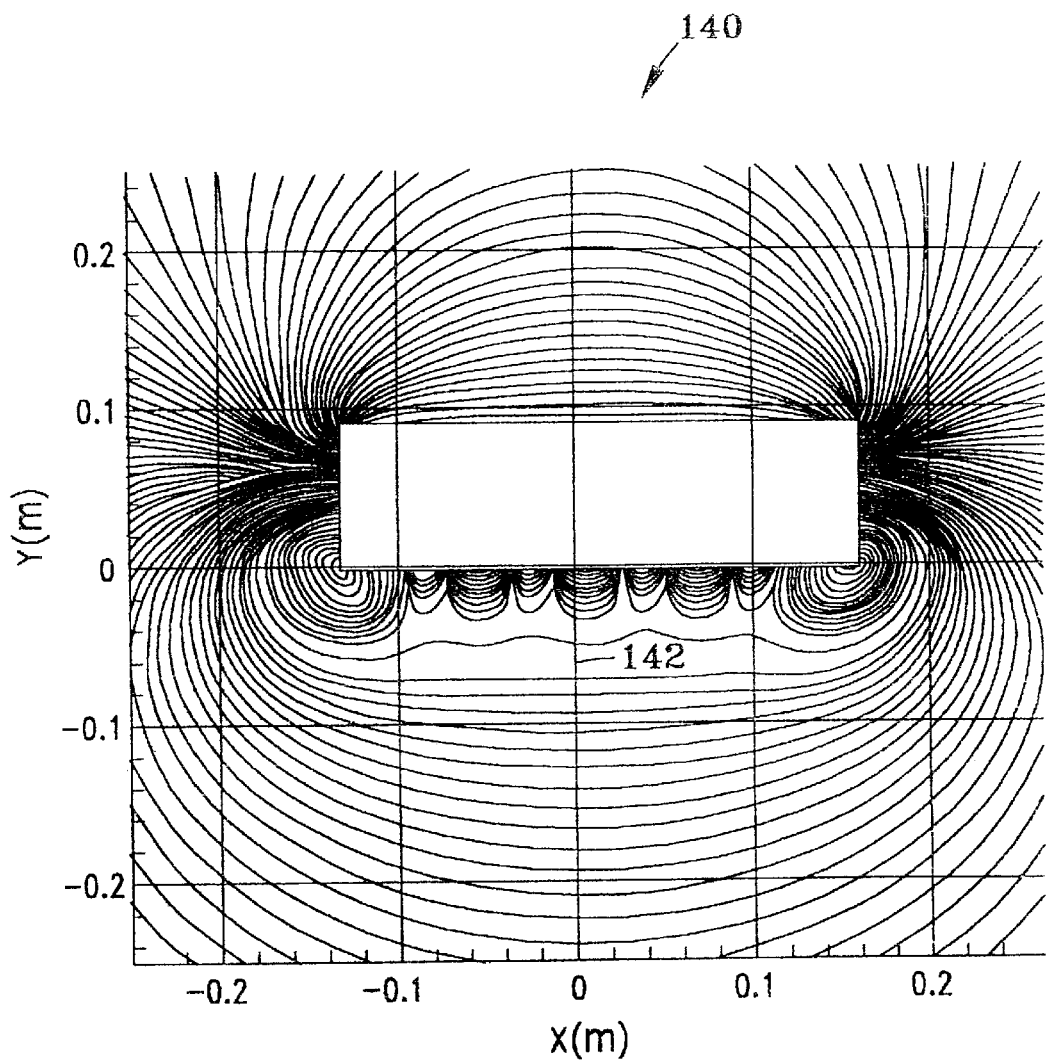
FIG. 8 is a diagram of a sensing field for a capacitance based proximity sensor shaped by sensor surface geometry.

FIG. 8 is a diagram of a sensing field 140 where the sensing surface has been shaped using sensor 90, as described above and shown in FIG. 5. In one embodiment, annular surfaces 92, 94, and 96 are optimized to flatten the field at a 5 cm distance. The field shown is more uniform compared to the field shown in FIG. 8, and is illustrative of an ability to customize field shaping by using segmented sensing surfaces. The circular construction used for field shaping can be extended to circular and cylindrical geometries (shown in FIG. 6).

Figure 9:
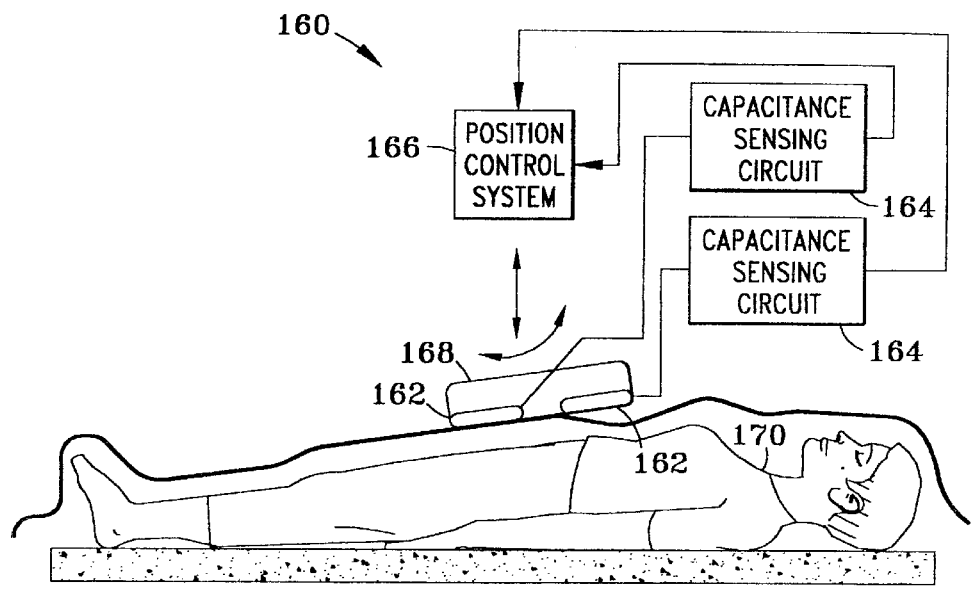
FIG. 9 is a diagram of a medical imaging system using capacitive based proximity sensors.

FIG. 9 is a diagram of a medical imaging system 160 using capacitive based proximity sensors 162 electrically connected to capacitive sensing circuits 164. Capacitive sensors 162 also provide a non-contact method of measuring the relative capacitance of a human body covered in paper, plastic and clothing. Circuits 164 provide data to a control system 166 regarding position and orientation of component 168 relative to 170. Component 168 in one embodiment is a radiation source. Component 168 in an alternative embodiment is a detector. Component 168 in a further alternate embodiment is a sensor. Component 168 in a still further embodiment is a nuclear medicine imaging source. Component 168 in another embodiment is a laser source. Component 168 in yet another embodiment is a component of a medical system, e.g., computer aided tomography (CAT), magnetic resonance imaging (MRI), computed tomography (CT), digital fluoroscopy, positron emission tomography (PET), positron emission transaxial tomography (PETT), and mammography. Although not shown in the figure, system 166 controls elevation, longitudinal movement and horizontal orientation of component 168. By using a capacitive based proximity approach, system 166 is configurable to follow the contours of an object, such as a body 170. System 166 can then be programmed to optimize the trajectory of component 168 relative to the object 170. In an exemplary embodiment, system 166 reduces exposures to radiation to body 170 compared to known systems, which either do not change the radiation source, detector elevations, or employ sensing devices, and which require a touching of body 170 before a control system adjusts movement of component 168.

Figure 10:
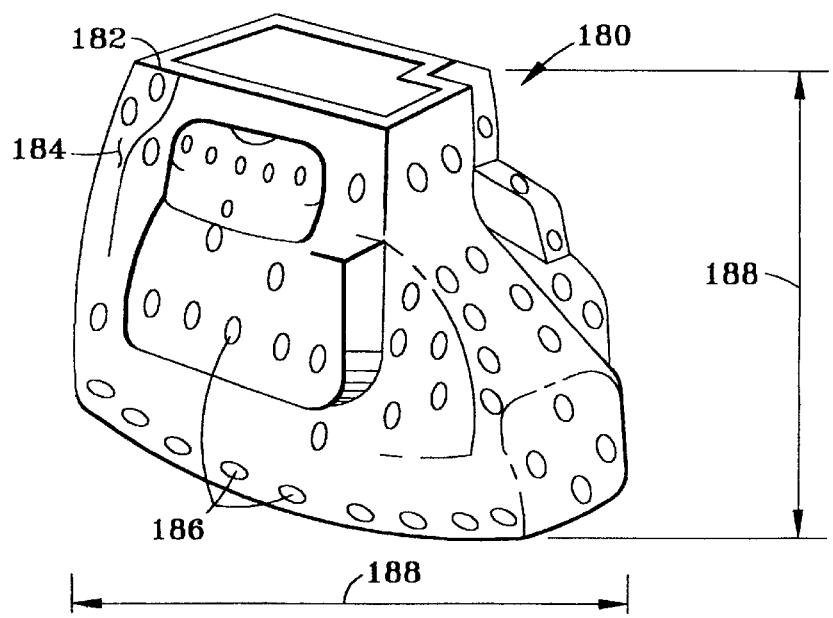
FIG. 10 is an illustration of an irregularly shaped apparatus with an outer surface covered with sensing material.

FIG. 10 is an illustration of an irregularly shaped apparatus 180 with an outer surface 182 covered with sensing material 184. Sensing material 184 is fabricated from a thin-film conducting material, e.g., aluminum, copper or tin. In an exemplary embodiment, thin-film sheets of copper foil are joined together with conductive epoxy 186. In one embodiment, the copper foil is 25 um in thickness. In an alternative embodiment, the thin-film sheets are fabricated by "spray depositing" a film of conductive material, e.g., tin, to a backing surface. Sensing material 184 is bonded to a backing surface (not shown). In an alternative embodiment, apparatus 180 is configured to take any form and shape and is not limited to a certain size range. In addition, sensing material 184 is electrically coupled to a capacitive sensing circuit (not shown). Apparatus 180 has one sensing zone 188. In an alternative embodiment, sensing material 184 has a plurality of sensing zones 188. Sensing zone 188 is capable of measuring changes in capacitance, e.g., 15–30 femtoFarads. In one embodiment, sensing zone 188 is optimized for detecting predetermined objects at a specified distance. In an alternative embodiment, apparatus 180 includes a plurality of sensing zones, each sensing zone optimized to detect a predetermined object at a specified distance.

While the invention has been described in terms of various specific embodiments, those skilled in the art will recognize that the invention can be practiced with modification within the spirit and scope of the claims.

What is claimed is:

1. A medical imaging system comprising:
   a radiation source comprising at least one capacitance based proximity sensor;
   a capacitive sensing circuit;
   an object electrically coupled to said capacitive sensing circuit using a conductive strap; and
   a control system configured to control positioning of said radiation source and said proximity sensor based on an input received from said capacitive sensing circuit.

2. A system in accordance with claim 1 wherein said control system configured to orient said radiation source in at least one of a horizontal and a vertical direction.

3. A system in accordance with claim 1 wherein said proximity sensor configured to measure capacitance of said object.

4. A system in accordance with claim 1 wherein said proximity sensor configured to measure capacitance of said object, when said object is in direct contact with said sensor.

5. A system in accordance with claim 1 wherein said proximity sensor configured to measure capacitance of said object, when said object is in proximity of said sensor.

6. A system in accordance with claim 1 wherein said object is a human body said proximity sensor configured to measure changes in capacitance as said sensor follows the human body contour.

7. A system in accordance with claim 1 wherein said proximity sensor configured to detect capacitive changes omni-directionally.

8. A system in accordance with claim 1 wherein said proximity sensor configured to be re-calibrated based on at least one of a size, a shape, and a effective sensing surface of an object.

9. A system in accordance with claim 1 wherein said proximity sensor configured to be re-calibrated based on at least one of a temperature and a relative humidity of an environment in which said object is placed.

10. A system in accordance with claim 1 wherein said capacitive sensing circuit configured to use charge transfer technology.

11. A system in accordance with claim 1 wherein said capacitive sensing circuit configured to sense changes in capacitance of at least 15 femtoFarads.

12. A system in accordance with claim 1 wherein said object is a human body said capacitive sensing circuit configured to sense capacitive changes to said human body, when said human body is covered with at least one of paper, plastic, and clothing.

13. A system in accordance with claim 1 wherein said proximity sensor configured to measure changes in capacitance of said object, when said object moves.

14. A system in accordance with claim 13 wherein said object is a human body such that said sensor detects movement of a raised arm, a crossed leg, a finger wiggling, a toe wiggling, and torso motion.

\* \* \* \* \*